United States Patent [19]

Alani et al.

[11] 4,390,027
[45] Jun. 28, 1983

[54] APPLICATION UNIT FOR EPICUTANEOUS TESTING OR TREATMENT

[76] Inventors: Safwat D. Alani, Wiesdorfer Platz 52; Milhim D. Sellman, Postfach 10 11 66, both of D-5090 Leverkusen 1, Fed. Rep. of Germany

[21] Appl. No.: 245,644
[22] PCT Filed: Jul. 18, 1980
[86] PCT No.: PCT/SE80/00191
§ 371 Date: Mar. 19, 1981
§ 102(e) Date: Mar. 19, 1981
[87] PCT Pub. No.: WO81/00199
PCT Pub. Date: Feb. 5, 1981

[51] Int. Cl.³ .................................................. A61B 10/00
[52] U.S. Cl. ..................................... 128/743; 128/307; 604/307
[58] Field of Search ............... 128/743, 260, 261, 289, 128/293, 304, 306, 307

[56] References Cited

U.S. PATENT DOCUMENTS 3,703,890 11/1972 Saunders, Jr. ..................... 128/743
4,158,359 6/1979 Kurokawa et al. .................. 128/743
4,166,457 9/1979 Jacobsen et al. ............... 128/207.21

FOREIGN PATENT DOCUMENTS 171095 10/1965 U.S.S.R. ............................ 128/743

Primary Examiner—John E. Kittle
Assistant Examiner—Nancy A. B. Swisher
Attorney, Agent, or Firm—Berman, Aisenberg & Platt

[57] ABSTRACT

The present invention relates to an application unit to be used for epicutaneous testing to clarify the etiology and diagnosis of allergic contact eczema and for the administration of therapeutically active substances for topical treatment of skin diseases, and comprising a carrier which consists a number of application devices each one of said devices is supplied with an application surface for one substance. The application device is composed of a nonabsorbent material. The said application surface is essentially located at the same level with the carrier's adhesive surface and is surrounded by an annular groove. The application units are covered by a covering layer which is provided with domes located above each application device and encompass the substances hermatically.

8 Claims, 4 Drawing Figures

APPLICATION UNIT FOR EPICUTANEOUS TESTING OR TREATMENT

DESCRIPTION

1. Technical Field

The present invention relates to an application unit which can be used for epicutaneous testing to clarify the etiology and diagnosis of allergic as well as light-potentiated contact eczema and for the administration of therapeutically active medicaments for treatment of local skin diseases or systemic ones.

BACKGROUND OF THE INVENTION

The epicutaneous test has been used for more than 70 years. The substance to be tested is applied on a patch and fixed to the skin with adhesive tape. The patch is left in place for 24 to 48 hours or more and then removed. If an eczematous response is elicited, the person probably has a contact allergy to the tested substance. Although always based on these principles, the testing procedures vary from one clinic to another. The conventional procedure of epicutaneous testing is very tedious and time consuming. Every patient has to be tested by the so-called "standard series" which is composed of about twenty allergens. Additional supplementary tests may be needed. The application of test substances on the patches is traditionally performed by hand. It is obvious that the procedure takes a very long time to achieve because the doses have to be dispensed as accurately as possible. Trying to be accurate in dosing, even when a trained staff is doing the work, is both tedious and tiresome. Accurate dosing is not possible by the conventional method however.

Patchtest technique has not as yet been subjected to systematic studies. There are no universally accepted procedures, test materials or norms for the concentration of test substances. Although the choice of suitable concentration of test substances is of fundamental importance, there are no universally accepted concentrations, and the concentrations differ from one clinic to another. The importance of standardized concentrations should be stressed upon since, for example, too high concentrations result in false positive reactions because of their primary irritant effect, and may even sensitize previously healthy patients, while too low concentrations produce false negative reactions.

Moreover, there are no norms for the vehicles in which the test substances are dissolved or norms for dosing the test substances which are applied on the patches.

In patch testing in test substances(allergens) applied are either (1) as they are or
(2) mixed with petrolatum or other ointment bases or
(3) dissolved in water, olive oil, alcohol, acetone, methylethylketone (MEK), isobutylketone, butyl—or ethylacetate or liquid paraffin.

Different vehicles may give different results. With identical concentrations of perfumes in vaseline and in water, positive reactions were more frequent with vaseline. Some ointment bases cannot efficiently release certain substances. Solutions evaporate easily and the concentration of the test substance increases, resulting in false positive reactions and the concentration becomes uncertain. Volatile substances tend to diffuse from ointment bases resulting in false negative reactions. Hygroscopic substances become diluted by atmospheric humidity so that the concentration decreases and moreover they may degrade during storage. Some substances may change and degrade when exposed to light.

In order to elicit an allergic reaction in an organism already sensitized, not only is the concentration of the allergen important but also the amount of the allergen per unit area of the skin. The strongest reactions are obtained with 35 $\mu$l of fluid. This is seldom taken in consideration which, from one clinic to another, vary considerably in size and hence also in the amount applied. The same thing i.e. not only the concentration, but also the amount per unit area can be of significance in inducing sensitization. It has been reported that the risk of patch-test sensitization increases with the amount of ointment or solution used. Moreover, large amounts of the allergen used may contaminate neighbouring test sites, giving rise to confusing test results.

Ointments for testing are kept either in glass jars or aluminium tubes.

The ointment dosages taken from the jars by a glass rod or expressed from aluminium tubes show striking degree of variation.

The amount of test solutions delivered by pipettes cannot be exactly measured and therefore show a great degree of variation. Application of too small doses of test substance must with certainty lead to false negative reactions; application of too large amounts may increase the risk of patch test sensitization.

Several materials, such as; linen, cotton and cellulose filter paper in different sizes, have been used. The size of the patch is not standardized. These test materials show up many disadvantages, for example the linen and cotton may react with the test substances, and the cellulose filter paper proved to reduce readily-oxidizable compounds, such as reduction of a hexvalent chrome(allergen) to the trivalent form(non-allergen) in a very short time.

Consequently, it may happen that a patient with chrome allergy does not react by a chrome patch test and is therefore declared free from chrome allergy.

Another disadvantage of the manual procedure of application of test substances from jars and tubes is that the order of tests should always be remembered. Not infrequently this order is being disturbed by the busy staff, giving rise to faults in the interpretation of test results and consequently to a wrong diagnosis. This serious fault may be suspected by the dermatologist when his clinical findings differ from the test results. This means that the tests have to be repeated. If the fault is not discovered then the problem is unsolved. The patient will avoid contact with wrong allergens and keep in contact with the actual ones. Medico-legal and compensation conflicts are to be expected in such cases.

The size of test area according to conventional testing methods varies considerably. It is about 1 cm or more in diameter. A large area of the skin is therefore needed to apply the "standard series" of about twenty test substances. Thus, a limited number of test substances can be tested. Additional tests cannot be performed without waiting for the recovery of the skin which has been previously tested.

When fixing the conventional patches onto the skin by adhesive tapes, it is usually difficult to keep them fixed because of sweating and body movement. Therefore, the necessary proper contact of test substances with the skin for 2 or more days is not alway successful. Tests are therefore often repeated.

The risk of exacerbation of the eczema during epicutaneous testing is common because the size of test area is too large. The test is also a tedious procedure.

Test patches of different kinds are already known through patent literature. They comprise a carrier with one or more places for the test substances. In the case where the carrier is provided with a test substance for later use, a covering film is applied on that carrier which hermatically encloses the substance. The covering film is removed immediately before the test patch is applied on the body.

A disadvantage with this type of carrier is that when the covering film is peeled off a larger or smaller portion of test substance follows with the protective film and this seriously affects the test result because it depends on an exact amount of test substance on an exactly defined surface. In order to solve this problem it even been suggested to apply the test substance on a tape and cover the substance with a piece of gauze or the like, whereby the test substance diffuses through the test patch when it is pressed against the body. This type of test patch requires special packing which protects the test substances together with the piece of gauze already applied on it. This makes the test device considerably more expensive especially when every single test substance must be packed separately.

Another drawback by the already used testpatches is that they do not accurately demarcate an exactly defined skin area, because the test substance tends to spread widely outside the carrier's test area. In the case where the carrier is gummed, even the adhesive layer would induce skin irritation, which would be difficult to differentiate it from the test reactions. One had tried to solve this problem by placing the test substances in tiny shallow covers which are fastened onto the skin by means of a tape. By this idea it was intended to press the cover's edge onto the skin and thereby limit the test area. But in practice it has been shown that the object could not be achieved without the use of a very strong adhesive, which normally gives rise to skin irritation. Moreover, these covers have shown up the same handicaps as mentioned before concerning the dosing, transport and storage of the testpatches.

THE OBJECT OF THE INVENTION AND THE MOST IMPORTANT CHARACTERISTICS

The object of the present invention is to eliminate the above-mentioned disadvantages and handicaps, and to bring about an application unit which permits an exactly dosed quantity of test substance, applied onto an accurately defined skin surface which is so confined that the test substance cannot spread outside the defined test surface, and without exposing the skin area in the neighbourhood for irritation by the carrier's adhesive or the like.

Another object of the present invention is to bring about an application unit which is simple in its construction and inexpensive. Still another object of the invention is that the application unit is provided with such a protective packing that it should neither be contaminated by the test substances when the packing is peeled off, nor by any other means the quantity of the test substance and/or the test surface be altered. This task has been achieved by means that the carrier comprises at least one application device which is provided with an application surface to keep one test substance.

The said application device is made of a non-absorbant impermeable durable sheet. The application surface is essentially located at the same level with the adhesive surface of the carrier, and is surrounded by an annular groove. And the covering layer is, in the middle of each application surface, provided with domes which are so dimensioned that with a distance compass the test substances.

According to the present invention, the dosing of the test substances(allergens) can be accomplished with a high degree of accuracy by means of manually or electrically driven dispensers.

The dose of test substances needed to elicit an allergic reaction could be reduced by using special vehicles and additives which increase skin permeability for the test substances, whereby the risk of sensitization or poisoning would be much reduced. By using the new test units, not only will the doses of the test substances always be constant but also the size of the test area of the skin, which adds additional accuracy on the test results.

According to the present invention petrolatum is a suitable vehicle for the test substances, which is proved to be the ideal base for the manufacturing of ointments for epicutaneous testing. When the substances show low permeability through the skin, one could add special additives which have the power to permeate through the skin to lead the test substance to the deeper skin layers.

By an industrial manufacturing of the application units according to the present invention, the concentration of the test substances(allergens) will always be the same and according to the latest established norm system. The concentration of the test substances will also be kept constant since the test surfaces with the test substances can effectively be sealed up, so that evaporation, oxidization and the effect of humidity and light would be prevented.

Newly prepared test substances applied onto the test devices of the test units are covered by a protective layer with domes, made for example of plastic. The units are then packed in a suitable way, for example in an aluminium or plastic film to protect the said units from environment. The stability of the test substances can therefore be guaranteed for a longer time.

According to the present invention the application of a test unit comprising, for example, a whole series of twenty test substances would only take a few seconds instead of, as conventionally performed, an extensive contribution. No trained staff is needed. The packing of several test units is easy to open and the patches are ready to apply onto the skin without additional preparation. By the same staff and time span more patients can be tested in the hospitals when the new test units are used. Moreover, the dermatologists, which normally do not perform epicutaneous testing in their own clinics, would find the procedure so easy and quick that they prefer to do it themselves.

The order of the test substances can not be disturbed since it is controlled during manufacturing so that the same order is always maintained. The test devices are numbered in each unit and every number represents a test substance.

According to the present invention the size of the test area is reduced to less than 1 cm in diameter. This reduction in size and the special construction of the test units permit a complete shutting off between the individual test devices, which makes the distance between the test devices be reduced. Moreover, the test units because of their reduced test surface, can be better fixed onto the skin. The test reactions will be smaller in size due to smaller size of test areas, causing the patient less suffering and also reduce the risk of exacerbation of the eczema and sensitization. A higher number of additional tests can be performed without waiting for the recovery of the skin which has been previously tested.

The majority of the dermatologists are not always willing to perform epicutaneous testing in their own clinics partly because they must spend a long time for every test, partly because a trained staff is important to perform the test effectively and partly because special equipment and test substances are required. Moreover, fresh test substances have to be maintained and this is very expensive.

The present invention assures better stability of the test substances(allergens) because of the nature of the carrier's material, the protective layer covering the test substances, and the outer packing of the test unit. For the same reason, the volatile test substances would not disappear from the test units. These test units therefore are very economical for both hospitals and private clinics.

By using the new test units there will be no need for any special equipment or room. All this tedious work to prepare the test patches according to the conventional procedure is unnecessary. All that is required is to open the packing and the test units are they are ready to be fixed onto the skin.

The basic idea of the present invention can also be utilized for treatment with therapeutical agents, such as antibiotics, corticosteroids and hormones, in order to treat local skin diseases or to administer through the skin therapeutical agents for the treatment of systemic diseases. The therapeutical agent, either pure, mixed with an ointment base or as solution, is applied onto the device of the test unit, then the unit is fixed on that part of the skin which is to be treated.

In such cases, where the treatment of skin diseases requires a potent therapeutical agent, such as corticosteroids, it is preferred to avoid unnecessarily overtreating the diseased skin and particularly to avoid consuming large quantities of the drug, because undesirable and even dangerous side effects may arise from absorption of the drug through the skin. Many cases have been reported about the side effects of corticosteroids in children because of indiscriminate use of high doses of corticosteroid ointments for the treatment of localized eczema. The steroids are absorbed through the skin, reaching the bloodstream and may give rise to systemic intoxication. Not only corticosteroids but also other drugs may give rise to dangerous and fatal intoxication through this route. By using a suitable size of the application units and their limiting grooves, the size and amount of the applied drug can be confined and controlled in each unit. More concentrated drugs can therefore be used for the treatment of obstinate cases of localized skin diseases, where the conventional concentration of the drugs is not effective. Examples for such diseases are skin cancer, melanoma, warts, chronic localized psoriasis, abscess, acne, haemangioma etc.

For systemic administration of drugs through the skin the drugs can be mixed with substances which increase the permeability of the skin for said drugs. Drug release from the mixture would be constant and prolonged. The drugs which usually irritate the stomach and intestines and those drugs which are destroyed by digestive enzymes are very good examples. The use of hormones is another example of usefulness of the application units of the present invention.

The administration is usually preferred to be prolonged. Depot hormone injections have been utilized in the treatment of menstrual disturbances and the menopause. The search after anticonceptional hormone treatment with prolonged effect is still going on. Digitalis and similar derivatives which are used for the treatment of heart diseases, also nitroglycerine and its derivatives which are used for the treatment of angina pectoris, and even diuretics and antidiabetics can be administered with the help of the present invention. The degree of absorption of the drugs can be regulated by means of varying the concentration of the drugs and modification of the type of the vehicle used so that an optimal release of the drug with prolonged high concentration level in the plasma is obtained in each special case.

DESCRIPTION OF THE DRAWINGS

Some executed examples of the application unit according to the invention are described with reference to the accompanying drawings.

DESCRIPTION OF THE PREFERRED EMBODIMENTS

Figure 1:
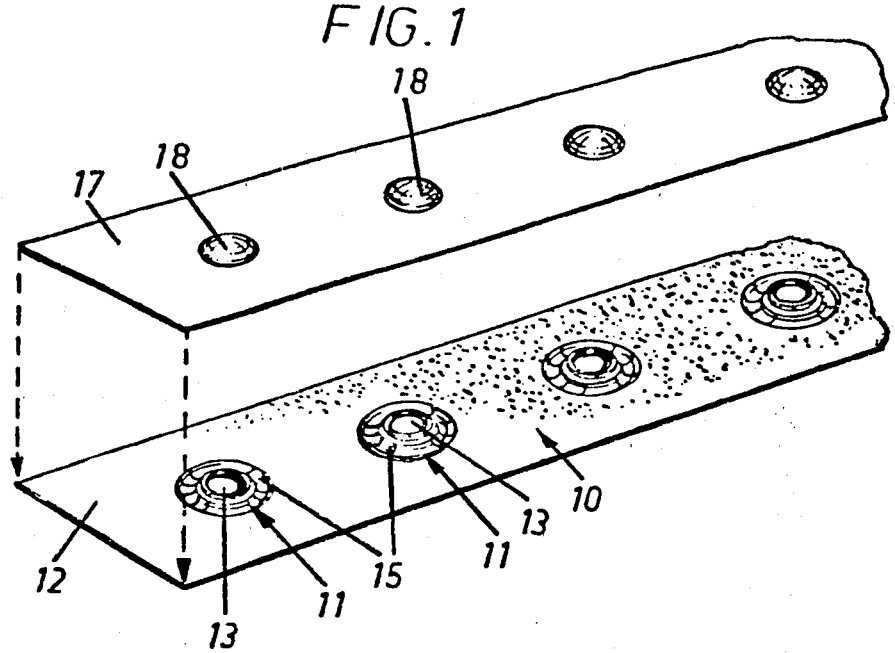
FIG. 1 comprises an exploded perspective view of the application unit of the present invention.
Figure 2:
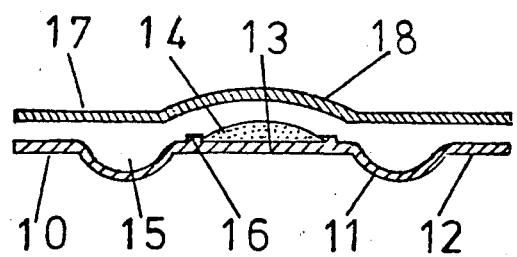
FIG. 2 comprises, in an enlarged scale, a sectional elevational view of the application unit according to FIG. 1.
Figure 3:
FIG. 3 comprises, in a smaller scale, a sectional view of the application unit in its position during use i.e. applied on the skin.

The application unit shown in FIGS. 1-3 comprises a carrier 10 provided with at least one, or preferably a number, for example 20, application devices 11. In the shown embodiments the carrier 10 and the application device are combined in one unit of a nonabsorbent impermeable material, for example plastic, plastic-treated paper or textile, metal film or the like. On one side of the carrier 10 and outside the application device 11 is applied an adhesive material or the like forming a continuous adhesive surface 12. Every application device 11 comprises an application surface 13 for one substance 14, for example test substance, therapeutical medicament or the like. The application surface 13 is surrounded by an annular groove 15, which extends in a direction from the application surface. The application surface 13 is placed essentially in the same level as the adhesive surface 12. The application surface 13 can eventually be surrounded by a very low peripheral edge 16, in order to facilitate the dispensing of the substance 14 and to limit its outspreading.

In order to protect the substance 14 during transport and storage the adhesive surface 12 is fitted with a covering layer 17 made of durable material which in the middle of every application device 11 is provided with a dome 18. The said dome is so dimensioned that it compasses the substance 14 with a distance to prevent contact with said substance. The dome 18 is so arranged that it compasses also the application surface 13.

The substance 14, which could be in ointment or cream form or the like, is applied on the application surface 13 with high accuracy concerning both the quantity and extension. The application of a test unit of for example 20 different test substances is done by peeling off the cover layer 17 from the carrier 10, after which the test unit is ready to be applied directly onto the skin.

Figure 4:
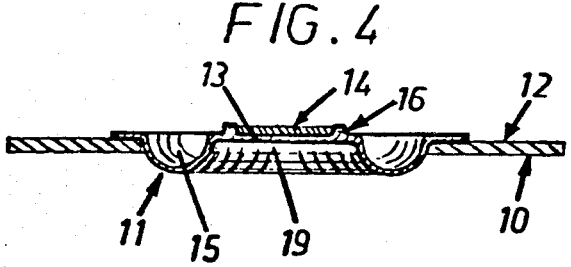
FIG. 4 comprises a sectional view of a modified form of the unit according to the invention.

The skin and the underlying tissue layers usually expand into the ring-formed groove 15, whereby every section which is exposed to the substance 14 would be a sharply-defined skin unit. The demarcation has been achieved without exercising pressure on the skin and thereby no impaired blood supply to the test area would occur. Because the application surface 13 is located in the same level with the adhesive surface 12, the substance 14 should certainly come in contact with the skin even if the substance is found in thin layer. The modified form of the unit shown in FIG. 4 differs from that unit described in FIGS. 1–3 by that every individual application device 11 constitutes a separate part by itself which is placed on or in a recess 19 in the carrier 10, which carrier can be made of an adhesive tape or the like. The test substance is protected by the same way as in the former examples by means of a durable cover layer 17.

The present invention is not limited to the shown preferred embodiment but also several variations and combinations among them are conceivable without departing from the spirit and scope of the invention.

We claim:

1. An application unit comprising:
   (a) a substantially planar carrier with an adhesive surface and at least one application device and
   (b) a covering layer substantially coextensive with the carrier, each application device consisting of a durable sheet made of nonabsorbent, impermeable material and
   (c) an application surface for one substance in substantially the same plane as that of the carrier and
   (d) an annular groove surrounding and extending from the application surface in a direction opposite that of the adhesive surface; the covering layer being substantially planar, but having an elevated area corresponding to each application surface and projecting in a direction opposite that of the annular groove.

2. An application unit according to claim 1 wherein each application surface has a peripherally-located projecting edge which extends in a direction opposite that of the annular groove.

3. An application unit according to claim 1 wherein the covering layer is adhered to the carrier and each elevated area of said covering layer is directly opposite a corresponding application surface.

4. An application unit according to claim 3 wherein at least one application surface has a test substance thereon.

5. An application unit according to claim 3 wherein at least one application surface has a medicament thereon.

6. An application unit according to claim 3 wherein each application surface has a peripherally-located projecting edge which extends in a direction opposite that of the annular groove.

7. An application unit according to claim 6 wherein each application surface contains a quantity of substance equivalent to one dose for a single test or for a single treatment.

8. An application unit according to claim 3 wherein each application surface contains a quantity of substance equivalent to one dose for a single test or for a single treatment.

* * * * *